(12) United States Patent
Huber et al.

(10) Patent No.: US 12,312,298 B2
(45) Date of Patent: May 27, 2025

(54) METHOD FOR MAKING ALDEHYDES, ALCOHOLS, AMIDES, AND CARBOXYLIC ACIDS FROM PLASTIC PYROLYSIS OIL

(71) Applicant: Wisconsin Alumni Research Foundation, Madison, WI (US)

(72) Inventors: George Huber, Middleton, WI (US); Houqian Li, Middleton, WI (US); Jiayang Wu, Madison, WI (US); Clark Landis, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 18/334,815

(22) Filed: Jun. 14, 2023

(65) Prior Publication Data

US 2024/0158324 A1 May 16, 2024

Related U.S. Application Data

(63) Continuation of application No. 18/051,685, filed on Nov. 1, 2022, now abandoned.

(51) Int. Cl.
| | | |
|---|---|---|
| *C07C 27/08* | (2006.01) | |
| *B01J 23/46* | (2006.01) | |
| *B01J 23/75* | (2006.01) | |
| *C07C 209/24* | (2006.01) | |

(52) U.S. Cl.
CPC ............. *C07C 27/08* (2013.01); *B01J 23/464* (2013.01); *B01J 23/75* (2013.01); *C07C 209/24* (2013.01)

(58) Field of Classification Search
CPC ...... C07C 27/08; C07C 209/24; B01J 23/464; B01J 23/75
See application file for complete search history.

(56) References Cited

U.S. PATENT DOCUMENTS

2022/0098491 A1 3/2022 Abbott et al.

FOREIGN PATENT DOCUMENTS

WO WO 2022/084238 A1 4/2022

OTHER PUBLICATIONS

Boy Cornils, Wolfgang A. Herrmann, Chi-Huey Wong, Horst Werner Zanthoff: Catalysis from A to Z: A Concise Encyclopedia (5th Ed.), Verlag Wiley-VCH Verlag GmbH & Co. KGaA, (2020), ISBN 978-3527343119. (Book—No Copy Provided).
Geyer, R.; Jambeck Jenna, R.; Law Kara, L. (2017) "Production, Use, and Fate of all Plastics ever Made," Science Advances 3(7):2.
Li, H., Huber, G. W., et al. (Sep. 14, 2022) "Expanding plastics recycling technologies: chemical aspects, technology status and challenges," Green Chemistry, Advance Article.
Makado, Gouki; Morimoto, Tsumoru; Sugimoto, Yasuko; Tsutsumi, Ken; Kagawa, Natsuko; Kakiuchi, Kiyomi (Feb. 15, 2010) "Highly Linear-Selective Hydroformylation of 1-Alkenes using Formaldehyde as a Syngas Substitute," Advanced Synthesis & Catalysis 352 (2-3):299-304.
Ojima I., Tsai C.-Y., Tzamarioudaki M., Bonafoux D. (2000) "The Hydroformylation Reaction," Org. React. 56:1.
Ragauskas, A. J.; Huber, G. W.; Wang, J.; Guss, A.; O'Neill, H. M.; Lin, C. S. K.; Wang, Y.; Wurm, F. R.; Meng, X., New Technologies are Needed to Improve the Recycling and Upcycling of Waste Plastics. Wiley Online Library: 2021; vol. 14, pp. 3982-3984.
Robert Franke, Detlef Selent, Armin Börner (2012) "Applied Hydroformylation," Chem. Rev. 112 (11):5675-5732.

*Primary Examiner* — Sikarl A Witherspoon
(74) *Attorney, Agent, or Firm* — Joseph T. Leone; Yanjun Ma; DeWitt LLP

(57) ABSTRACT

A method to make primary alcohols, carboxylic acids, amines, and other value-added chemicals from plastic waste. The method includes the steps of pyrolyzing plastic waste to yield pyrolysis oil; hydroformylating the pyrolysis oil in the absence of any added co-reactants to yield a mixture comprising aldehydes; and hydrogenating, oxidizing, aminating, or aldolizing the mixture to yield a product comprising primary alcohols, carboxylic acids, amines, or larger (>C10) chemicals with carbonyl function groups.

8 Claims, 14 Drawing Sheets

METHOD FOR MAKING ALDEHYDES, ALCOHOLS, AMIDES, AND CARBOXYLIC ACIDS FROM PLASTIC PYROLYSIS OIL

CROSS-REFERENCE TO RELATED APPLICATIONS

This is a continuation of co-pending application Ser. No. 18/051,685, filed Nov. 1, 2022.

FEDERAL FUNDING STATEMENT

This invention was made with government support awarded under DE-EE0009285 awarded by the US Department of Energy. The government has certain rights in the invention.

BACKGROUND

Plastics have revolutionized our society, allowing us to inexpensively make a variety of materials that have a myriad of uses throughout industry. The first three synthetic plastics were polystyrene (PS) in 1839, polyvinyl chloride (PVC) in 1835 and Bakelite in 1907. Industrial plastic production began to expand in earnest around 1950 when global plastic production reached 2 million tons/yr. (Geyer, R.; Jambeck Jenna, R.; Law Kara, L. (2017) "Production, Use, and Fate of all Plastics ever Made," *Science Advances* 3(7):2. Current (2021) global plastic production is around 380 million tons/yr.

Currently, forty percent (40%) of waste plastic is landfilled. Only fourteen percent (14%) of waste plastic is burned for energy recovery. While this does not create a solid waste problem, it does generate greenhouse gases. Another fourteen percent of waste plastics are currently "recycled" or repurposed in some form, with 8% being "cascaded recycled" to lower quality materials. Only 2% of plastics are currently used in closed-loop recycling where virgin plastics can be used. The percentages of plastics recycled in any fashion varies greatly, country-to-country—with the U.S. currently recycling roughly 10% of its waste plastic and the EU recycling roughly 31% of its waste plastics. Ragauskas, A. J.; Huber, G. W.; Wang, J.; Guss, A.; O'Neill, H. M.; Lin, C. S. K.; Wang, Y.; Wurm, F. R.; Meng, X., New Technologies are Needed to Improve the Recycling and Upcycling of Waste Plastics. Wiley Online Library: 2021; Vol. 14, pp 3982-3984.

The low amount of recycled plastics is due to several reasons including: 1) plastics have a wide variety of compositions, 2) the high cost of collecting and sorting different types of plastics, especially the removal of contamination, and 3) the high capital costs and technological uncertainties of more "advanced recycling options." Recent changes in legislation along with the desire from consumers for more sustainable products has created a dramatic push by industry for more advanced plastic recycling technologies. IHS Markit has projected that $300 billion of capital spending that is earmarked for new plastic production capacity should be redirected to plastic recycling technologies to meet circular economy goals.

U.S. Published Patent Application 2022/0098491, published Mar. 31, 2022, describes a process for making chemicals that can be certified as "circular" according to International Sustainability and Carbon Certification (ISCC) standards. Thus, in this context, "circular" denotes that the chemical has been regenerated or reclaimed from spent material—for example regenerating ethylene from poly(ethylene) waste. The process hinges upon striking a mass balance at every step of the process so that the amount of recycled material can be tracked. Disclosed is a process for producing chemicals or polymers from plastic waste, wherein the process comprises (a) providing a pyrolysis oil from plastic waste, wherein the pyrolysis oil comprises light (C2-C5) hydrocarbons and heavy (C6+) hydrocarbons; (b) separating at least a portion of the pyrolysis oil into a pyrolysis gas stream comprising light (C2-C5) hydrocarbons and a pyrolysis liquid stream comprising the heavy (C6+) hydrocarbons; (c) optionally, providing a petroleum-based, fossil fuel-based, or bio-based feed; (d) introducing one or more primary processing unit feeds, each comprising independently, [1] the pyrolysis gas stream, the pyrolysis liquid stream, the pyrolysis oil, or any combination thereof, and [2] when present, the petroleum-based, fossil fuel-based, or bio-based feed, each at a known feed rate, into one or more primary processing units, thereby providing one or more primary processing unit feeds, each comprising at least a portion of the pyrolysis oil in a known concentration; and (e) converting the one or more primary processing unit feeds into one or more primary processing unit output streams, a portion of each output stream comprising at least one circular product, wherein the weight or the fraction of each circular product attributable to the pyrolysis oil or plastic waste is determined by mass balance.

Several additional technologies currently exist to chemically recycle plastics. Plastics undergo thermal degradation to produce a liquid known as pyrolysis oil. Autothermal pyrolysis can reduce the heat required for pyrolysis by adding a certain amount of oxygen although the technology is still not mature. (Li, H., Huber, G. W., et al. (14 Sep. 2022) "Expanding plastics recycling technologies: chemical aspects, technology status and challenges," *Green Chemistry*, Advance Article. Pyrolysis oil can be converted into aromatics and olefins by either steam cracking or using a form of catalytic upgrading as noted above. This produces aromatics and olefins which can then be re-used to make new recycled plastics that have the same properties as the virgin plastics.

Multilayer-plastics can be processed via dissolution-based recycling approaches generating pure plastic flakes which can then be re-extruded into recycled plastic resins. Polyesters and polycarbonates can be chemically or enzymatically converted into their monomers by methanolysis and other technologies. These monomers can then be re-used to remake the polymers. Plastics can also be gasified to synthesis gas which can be used to make methanol or transportation fuels. Methanol can then be converted into aromatics and olefins. None of these approaches, however, has been widely implemented due to various economic and technical difficulties.

There thus remains a long-felt and unmet need to generate value-added chemicals from waste plastics.

SUMMARY OF THE INVENTION

Disclosed herein is a method to make value-added chemicals from plastic waste. The method comprises providing pyrolysis oil from plastic waste, where the pyrolysis oil comprises olefins; and then hydroformylating the pyrolysis oil, in the absence of any added co-reactants and solvents, wherein at least a portion of the olefins in the pyrolysis oil are converted to aldehydes, to yield a mixture comprising aldehydes. Then at least a portion of the mixture of is subjected to a reaction selected from the group consisting of (i) hydrogenation to yield a product mixture comprising a product selected from the group consisting of primary alcohols, di-alcohols, esters, and combinations thereof, (ii) amination to yield a product mixture comprising amines, (iii) oxidation to yield a product mixture comprising carboxylic acids, and (iv) aldolization to yield a product mixture comprising aldehydes having a molecular weight greater than the aldehydes immediately after the hydroformylation step.

A specific version of the method is directed to making primary alcohols and di-alcohols, carboxylic acids, dicarboxylic acids, amines and di-amines from plastic waste. The method comprises providing pyrolysis oil from plastic waste, where the pyrolysis oil comprises olefins. The pyrolysis oil is hydroformylated, in the absence of any added co-reactants and solvents, wherein at least a portion of the olefins in the pyrolysis oil are converted to aldehydes. This yields a mixture comprising aldehydes. The pyrolysis oil is hydroformylated neat, without any co-reactants or added solvents. The mixture comprising aldehydes is then hydrogenated to yield a product mixture comprising a product selected from the group consisting of primary alcohols and di-alcohols and combinations thereof. Alternatively, a range of chemistry can be done on the aldheydes. For example, the aldehdyes can be oxidized to carboxylic acids or aminated to amines.

The pyrolysis oil can originate from any waste plastic stream that yields a pyrolysis oil comprising olefins, such as (but not limited to) poly(alkylenes). Pyrolysis oil, as defined in this application, includes any liquid product produced from thermal depolymerization of plastics. The thermal depolymerization can include gas-phase pyrolysis, autothermal pyrolysis (where small amounts of oxygen are added to the pyrolysis reactor), liquid—phase thermal depolymerization, or water depolymerization with supercritical water.

The hydroformylation step is preferably performed by contacting the pyrolysis oil with syngas and a transition metal-containing catalyst. As noted above, hydroformylation may also be accomplished using formaldehyde, rather than syngas. The preferred catalysts comprise cobalt or rhodium. Suitable catalysts include, but are not limited to $HCo(CO)_4$, $Co_2(CO)_8$, a triphenylphosphine-modified cobalt-containing catalyst, a triphenylphosphine-modified rhodium-containing catalyst, a cobalt-containing salt of triphenylphosphinetrisulfonate, and/or a rhodium-containing salt of triphenylphosphinetrisulfonate.

The hydroformylation reaction may be carried out under any set of time, temperature, and pressure conditions that result in the hydroformylation of at least a portion of the alkenes present in the pyrolysis oil. In a preferred, non-limiting set of conditions, the hydroformylation is conducted at a pressure of at least 50 atm and at a temperature of at least 100° C.

The hydrogenation step can be completed using any set of reaction conditions and catalysts, now know or developed in the future, that result in the hydrogenation of aldehydes into alcohols. Exemplary conditions are shown in FIGS. 5A and 5B.

In another version of the method, the pyrolysis oil is separated (for example, via distillation) into a light cut having a boiling point less than about 175° C. and a heavy cut having a boiling point greater than about 175° C. The hydroformylation reaction and the hydrogenation reaction are then conducted separately on the light cut, the heavy cut, or both the light and heavy cuts, as described herein. Generally speaking, hydroformylation followed by hydrogenation of the light cut yields a product mixture comprising products having from about 5 to about 13 carbon atoms. When the same two reactions are performed on the heavy cut, the product mixture typically comprises products having from about 11 to about 30 carbon atoms.

In addition to hydrogenation other reactions can be done on the aldehydes. Amination of the hydroformylated pyrolysis oil will produce amines. Oxidation of the hydroformylated pyrolysis oils will produce carboxylic acids. These chemicals represent a tremendous product breadth and a huge market opportunity. Aliphatic alcohol, amine and carboxylates are directly employed in a broad range of applications. For example, low molecular weight water soluble alcohols are directly used as solvents for coatings, dyes, inks, plastic flavorings, perfumes, cosmetics, pharmaceuticals, cleaners and polishes. Higher molecular weight alcohols are used as latent solvents and coupling agents in coatings. Carboxylic acids are directly employed as stabilizers, plasticizers, coating additives, lubricants, pharmaceuticals, pesticides, food and food additives. Aliphatic primary, secondary and tertiary amines are employed as fabric softeners, froth flotation agents, corrosion inhibitors, lubricants, friction modifiers and components of cosmetic formulations.

Aliphatic alcohols, carboxylates and amines are valuable precursors for solvents and surfactants. For example, ethoxylated lower (e.g. $C_6$) alcohols are slow evaporating solvents that aids in coating film formation. Higher (commonly $C_{12+}$) alcohol sulfates are very widely used active ingredients of detergent products due to their wetting, cleansing and foaming properties. Alcohol ethoxylates and ethoxysulfates are also widely used in cosmetics, cleaning products, coatings and a host of other commercial products. Aliphatic acids are also ethoxylated to produce surfactants for both aqueous and oil media. They are skin friendly and therefore employed in cosmetics as well as a host of other applications such as textile processing, emulsifiers, cleaning agents, antistatic additives, fabric softeners, lubricants, metal working fluids and pharmaceutical formulations. Amine and fatty amine ethoxylates are nonionic surfactants resulting from the reaction of alkylamines with ethylene oxide. These surfactants are employed in oil and gas, crop protection and textile processing, as solubilizers, wetting agents, anti-corrosives and adjuvants. They show excellent solvency, low foam properties and chemical stability.

Phosphate ester surfactants, including ethoxylated alcohol phosphates, are versatile anionic surfactants employed in agricultural applications, emulsification, antistatic, corrosion inhibition and cleaning formulations. These are just a few leading examples of a tremendous variety of valuable specialty chemicals derived from fatty alcohols, carboxylates and amines.

Abbreviations and Definitions

All references to singular characteristics or limitations of the disclosed method shall include the corresponding plural characteristic or limitation, and vice-versa, unless otherwise specified or clearly implied to the contrary by the context in which the reference is made. The indefinite articles "a" and "an" mean "one or more."

All combinations of method steps disclosed herein can be performed in any order, unless otherwise specified or clearly implied to the contrary by the context in which the referenced combination is made.

The method disclosed herein can comprise, consist of, or consist essentially of the essential elements and steps described herein, as well as any additional or optional ingredients, components, or limitations described herein or otherwise useful in organic chemistry.

2D-GC=two-dimensional gas chromatography. HDPE=high-density polyethylene. PE=polyethylene.

The term "hydroformylation" is defined broadly herein to include any reaction that adds a hydrogen and a formyl group (i.e., an acyl group, —C(=O)H) to carbon-carbon unsaturated bonds, especially (but not limited to) the double bound of an alpha-olefin. Examples of hydroformylation reactions include the Oxo Process, which yields alkanals from 1-alkenes, typically using a cobalt or rhodium catalyst. As used herein, hydroformylation refers to any reaction that yields an aldehyde product from an alkene reactant. In the preferred implementation, the reaction proceeds using syngas (or formaldehyde in the presence of a homogenous, transition metal catalyst:

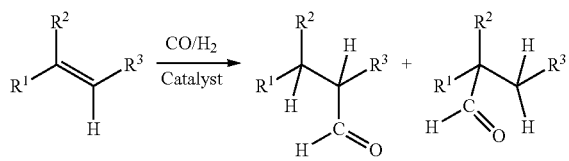

Hydroformylation reactions have been described extensively in the literature and will not be described in great detail herein. Preferred reaction conditions, though, are noted in the Detailed Description. See, for example, Robert Franke, Detlef Selent, Armin Börner (2012) "Applied Hydroformylation," *Chem. Rev.* 112 (11):5675-5732; Ojima I., Tsai C.-Y., Tzamarioudaki M., Bonafoux D. (2000) "The Hydroformylation Reaction," *Org. React.* 56:1; and Makado, Gouki; Morimoto, Tsumoru; Sugimoto, Yasuko; Tsutsumi, Ken; Kagawa, Natsuko; Kakiuchi, Kiyomi (15 Feb. 2010) "Highly Linear-Selective Hydroformylation of 1-Alkenes using Formaldehyde as a Syngas Substitute," *Advanced Synthesis & Catalysis* 352 (2-3):299-304.

There are several variations on the basic hydroformylation approach. The original process yields propionaldehyde (i.e., propanal) from ethylene and syngas using cobalt tetracarbonyl hydride as the catalyst. BASF-oxo process. The BASF-oxo process also uses cobalt carbonyl-based catalysts. The reaction is typically conducted at a pressure of about 30 MPa (about 300 atm) and a temperature of from about 150° C. to about 170° C. A related process, known as the Shell process, uses cobalt complexes modified with phosphine ligands to hydroformylate C7-C14 olefins. The resulting aldehydes are hydrogenated to the corresponding fatty alcohols. The process is generally conducted at a pressure of about 4 to about 8 MPa (about 40 atm to about 80 atm) and at a temperature of from about 150 to about 190° C. A low-pressure oxo process can be used to hydroformylate gases such as propylene. Here, a rhodium catalyst is dissolved in a high boiling point oil and the reactant is bubbled through the oil/catalyst solution. The process is carried out at a pressure of about 1.8 MPa (about 18 atm) and a temperature of from about 95° C. to about 100° C. See Boy Cornils, Wolfgang A. Herrmann, Chi-Huey Wong, Horst Werner Zanthoff: Catalysis from A to Z: A Concise Encyclopedia (5th Ed.), Verlag Wiley-VCH Verlag GmbH & Co. KGaA, (2020), ISBN 978-3527343119.

As used herein, the phrase "transition metal-containing catalyst" means any catalyst, now known or developed in the future, homogeneous or heterogeneous with the reactant(s), that comprises one or metals from Groups 3-12 of the periodic table of elements. Specifically included within the term are catalysts containing one or more transition metals selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, and uranium.

Cobalt- and rhodium-containing catalysts are preferred, although other transition metal catalysts may be used. Cobalt-containing catalysts are generally preferred from an economic perspective; rhodium catalysts are significantly more expensive than cobalt catalyst.

The term "poly(alkylene)" is used synonymously with "polyaklene" and "polyolefin" and refers to polymers having the general structure —[CH$_2$—CHR]n—wherein "R" is a linear, branched, or cyclic hydrocarbon. Examples of poly(alkylenes) include, but is not limited to poly(butylene), poly(butyl ethylene), poly(cyclohexylethylene), poly(ethylene), poly(heptylethylene), poly(hexylethylene), poly(isobutene), poly(isobutylethylene), poly(isopropylethylene), poly(2-methylbutene), poly(octylethylene), poly(pentylethylene), poly(propylene), poly(propylethylene), poly(tert-butylethylene), etc.

The term "pyrolysis oil" is used herein generically to denote the oily substance yielded by the thermal depolymerization of polymers in general and preferably from the thermal depolymerization of waste plastics. Thus, "pyrolysis oil" encompasses a product formed via pyrolysis itself, as well as other thermal depolymerization methods, with or without catalysis or chemical treatment, such as (but not limited to), catalytic depolymerization, hydrocracking (i.e., hydrothermal liquefaction), liquefaction with other, supercritical, non-aqueous solvents (i.e., non-aqueous solvolysis), steam cracking, and the like.

BRIEF DESCRIPTION OF THE DRAWINGS

FIG. 3A is the 2D-GC of the light cut.

DETAILED DESCRIPTION OF THE INVENTION

Figure 1:
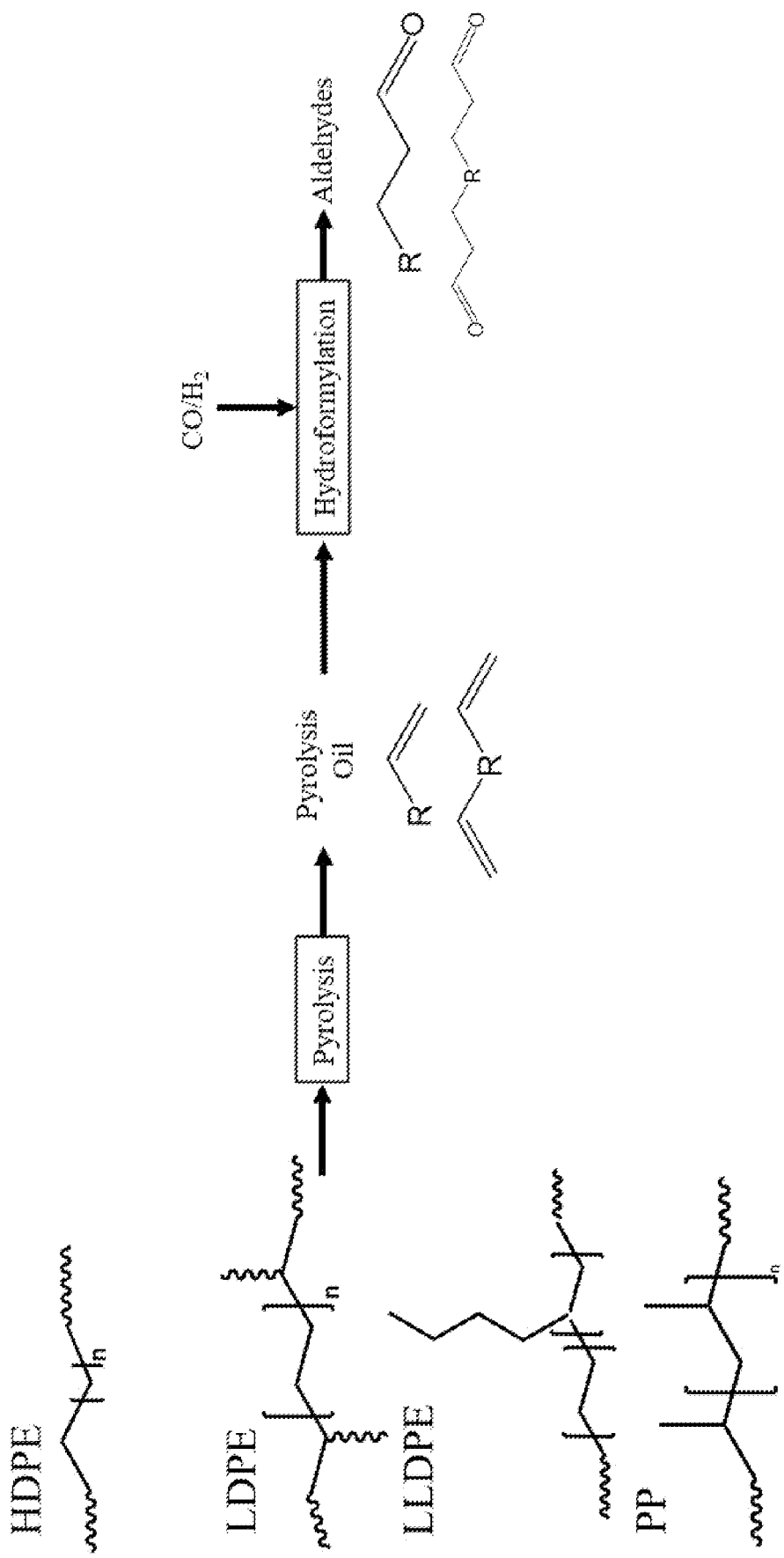
FIG. 1 depicts the crux of the method disclosed herein. Waste plastics (HDPE is shown as a non-limiting example) is pyrolyzed to yield pyrolysis oil. The 500° C. pyrolysis temperature is also exemplary. Pyrolysis temperatures above and below 500° C. are within the scope of the present disclosure. The pyrolysis oil is then subjected to hydroformylation using syngas (a mixture of carbon dioxide and molecular hydrogen) to yield a product mixture comprising aldehydes. The hydroformylation reaction conditions noted (120° C., for 3 hours, over a CO$_2$(CO)$_8$ catalyst) are exemplary and non-limiting.

Newly developed and disclosed herein is a method of making value-added chemicals, principally primary alcohols, di-alcohols, and esters, from a waste plastic feedstock. The heart of the method is illustrated in FIG. 1. As shown in the figure, post-consumer plastic waste is first subjected to pyrolysis (or other thermal depolymerization processing) to yield pyrolysis oil. The pyrolysis oil is then hydroformylated neat to yield a mixture comprising aldehydes. Surprisingly the aromatics, paraffins, and other impurities in the plastic pyrolysis oil did not cause inhibition of the hydroformylation catalyst. As shown in the figure, the plastic waste feedstock is designated as "Post-Consumer HDPE," that is, post-consumer, high-density poly(ethylene). This is an exemplary, non-limiting feedstock for the method. The incoming plastic feedstock may be any waste plastic stream (post-consumer or post-industrial), of any type of polymer or mixtures of polymers, that will yield a pyrolysis oil comprising olefins (i.e., alkenes). Likewise, "pyrolysis" is an exemplary, non-limiting type of thermal depolymerization that may be used to generate the pyrolysis oil. As noted above, the pyrolysis oil may also be generated by any other type of thermal/chemical/catalytic depolymerization of the incoming plastic feedstock.

The pyrolysis oil is then hydroformylated by contacting it with syngas in the presence of a transition metal-containing catalysts as described herein. As shown in FIG. 1, an exemplary catalyst, Co$_2$(CO)$_8$, was used. The hydroformylation reaction is carried out under time, temperature, and pressure values that yield a mixture comprising aldehydes. FIG. 1 shows exemplary condition of a reaction at 120° C., for three hours. The pressure, not indicated in FIG. 1, was about 70 bar.

Figure 2:
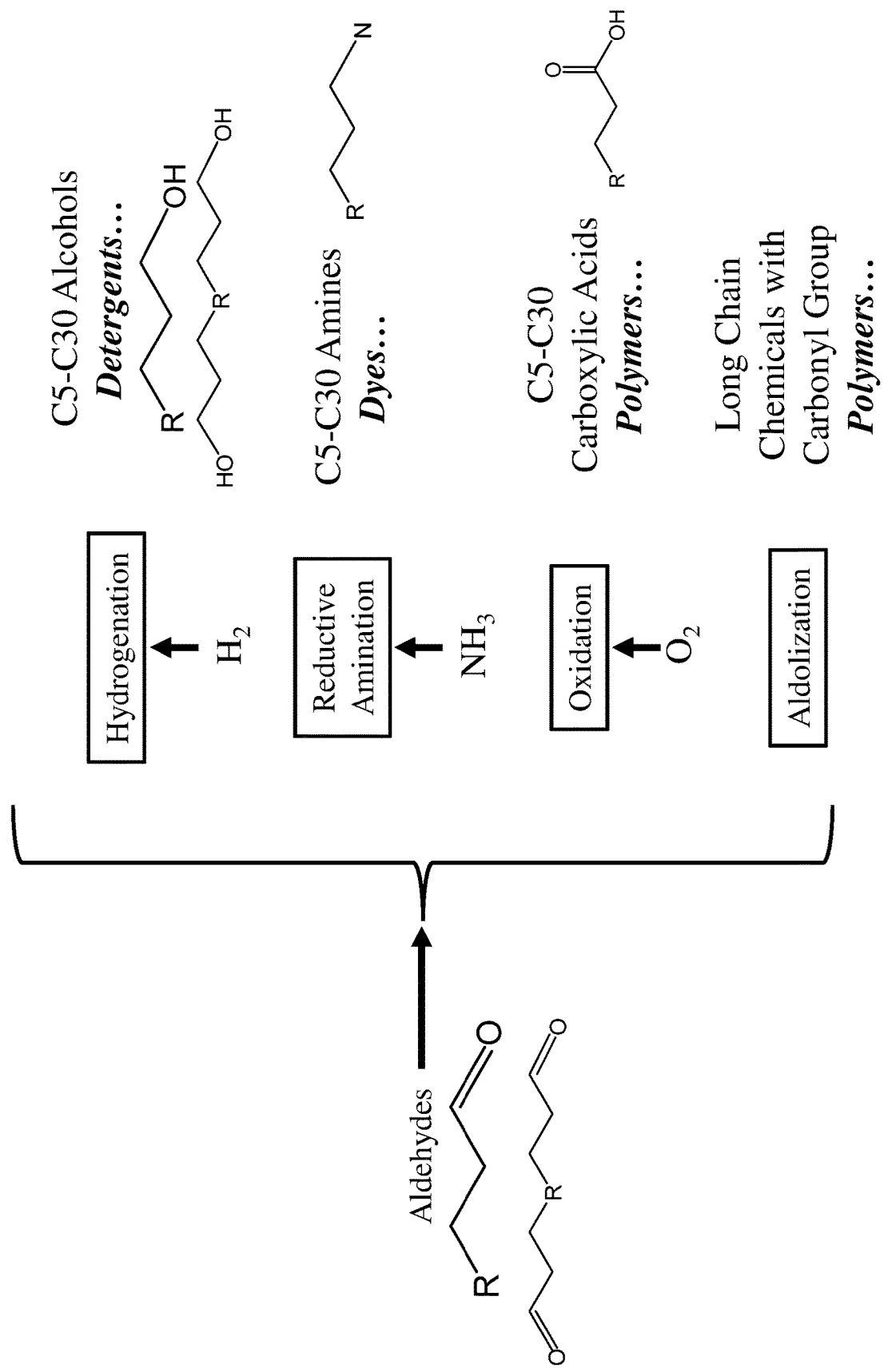
FIG. 2 depicts downstream additional, exemplary processing on the product mixture comprising aldehydes that results from the method depicted in FIG. 1. The exemplary reactions include (but are not limited to) hydrogenation, reductive amination, oxidation, and aldolization.

As shown in FIG. 2, the mixture resulting from the hydroformylation reaction is rich in aldehydes. These aldehydes can then be upgraded by any number of subsequent reactions to yield value-added chemicals. Thus, the mixture resulting from hydroformylation can be subjected to hydrogenation to yield alcohols, or reductive amination to yield amines, or oxidized to yield carboxylic acids, or subjected to an aldol reaction to yield new β-hydroxy and/or beta-unsaturated carbonyl compounds. Aldolization of the product mixture, post-hydroformylation, thus yields longer-chain polymers.

Figure 3A:
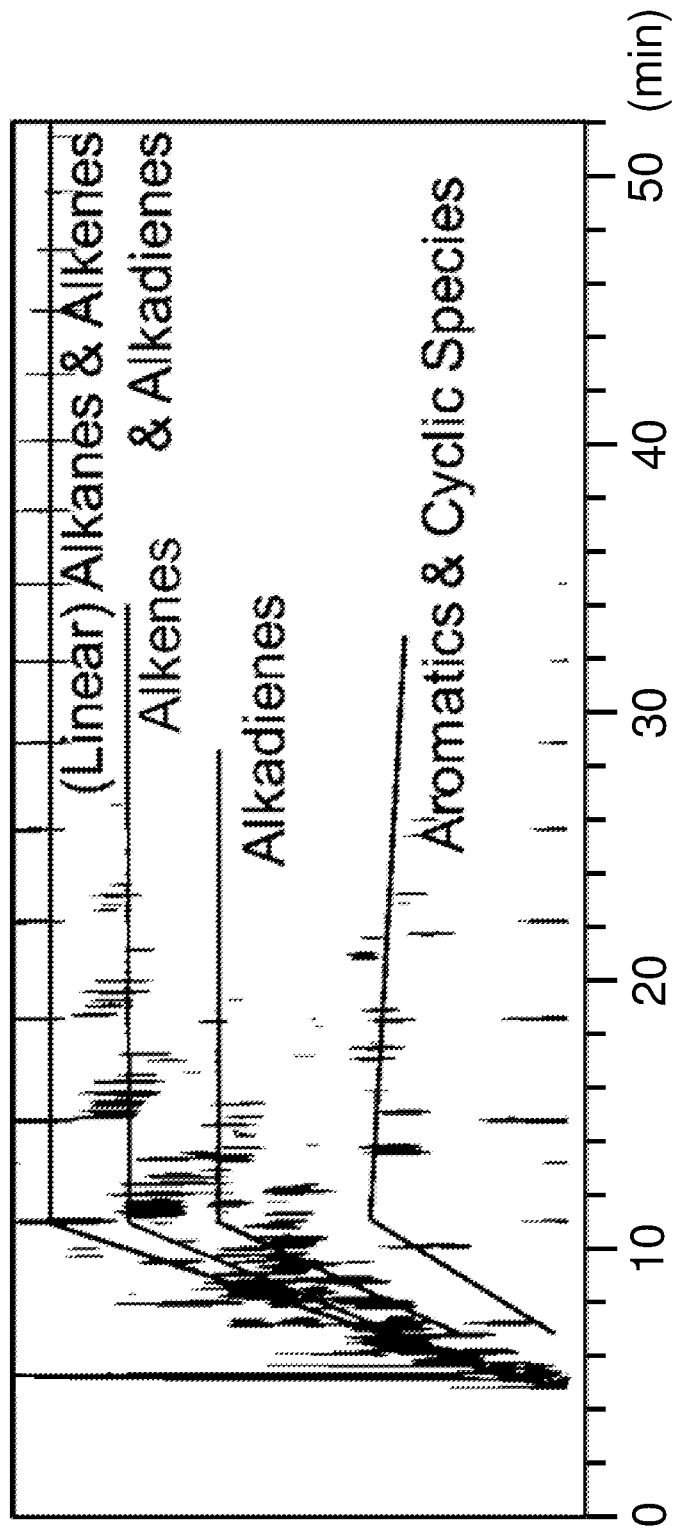
FIG. 3A is a two-dimensional gas chromatogram (2D-GC) of pyrolysis oil formed as in FIG. 1 and then distilled into a "light cut" having a boiling point less than about 175° C. (and comprising compounds having less than about 11 carbon atoms, i.e. <C11) and a "heavy cut" having a boiling point greater than about 175° C. (and comprising compounds having more than about 10 carbon atoms, i.e. >C10)

The hydroformylation reaction can be performed on the bulk pyrolysis oil neat—without any pre-reaction processing steps. Alternatively, the pyrolysis oil may be separated into light and heavy cuts via distillation (or any other suitable separation means). Thus, for example, the pyrolysis oil may be separated into a light cut that boils at a temperature less than about 175° C. and a heavy cut that boils at a temperature greater than about 175° C. This was done and the heavy and light cuts subjected to 2D-GC. The 2D-GC of an exemplary light cut pyrolysis oil, made from colored post-consumer waste HDPE and having a boiling point of about 175° C. is shown in FIG. 3A. As shown in chromatogram, the light cut includes linear alkanes, alkenes, and alkadienes (top trace), other (non-linear) alkenes (second trace from top), other (non-linear) alkadienes (third trace from top), and various aromatics and cyclic compounds (bottom trace).

Figure 3B:
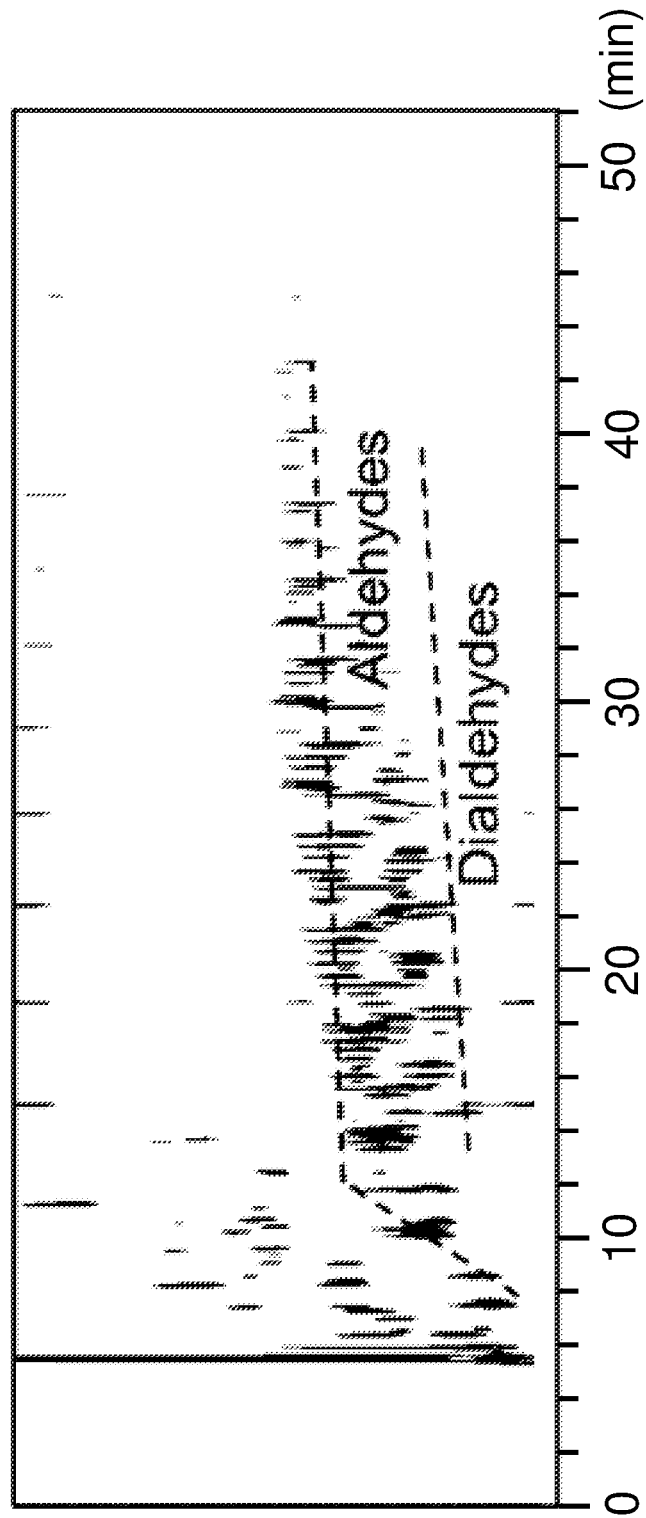
FIG. 3B is the 2D-GC analysis of the light cut oil analyzed in FIG. 3A after hydroformylation catalyzed by CO$_2$(CO)$_8$ in a 350 mL stainless steel batch reactor for 3 hours. Conditions: 120° C., 70 Bar Syngas (CO/H$_2$=1), 900 rpm, 10 wt % CO$_2$(CO)$_8$ in oil.

The light cut whose 2D-GC is shown in FIG. 3A was then subjected to hydroformylation in a batch reactor at 120° C., for 3 hours, with vigorous stirring (900 rpm) using CO$_2$(CO)$_3$ as the catalyst, with syngas (CO:H$_2$=1) at a pressure of about 70 Bar. The 2D-GC of the resulting product mixture is shown in FIG. 3B. As shown in FIG. 3B, the product mixture comprised aldehydes and dialdehydes. That is, at least a portion of the alkenes and alkadienes present in the original pyrolysis oil were converted to aldehydes and dialdehydes.

Figure 3C:
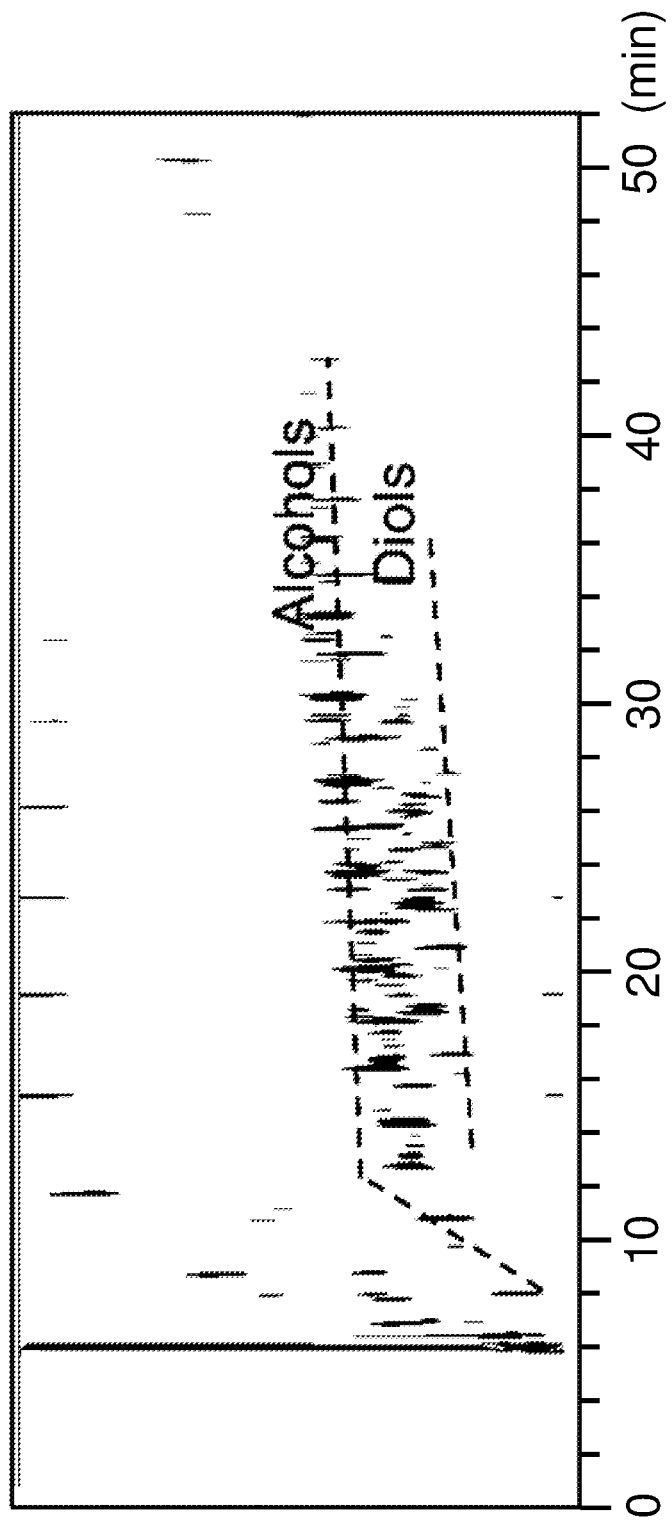
FIG. 3C is the 2D-GC analysis of the light cut oil from FIG. 3B after hydrogenation catalyzed by 20% Ni/SiO$_2$ in a continuous flow reactor for 5 hours. Conditions: 100° C., 78 Bar H$_2$, WHSV=1 hr$^{-1}$.

The mixture whose 2D-GC is shown in FIG. 3B was then subjected to hydrogenation after the removal of Co catalyst. The removal of Co catalysts was carried out in a 125 mL jar. The mixture (e.g., 10 mL) was stirred 6 hours exposed to air with a solution (e.g., 10 mL water, 0.5 g $Co(NO_3)_2 6H_2O$, and 1 mL acetic acid) under ambient conditions. The hydrogenation was then performed in a continuous flow reactor at 100° C., under 78 Bar of $H_2$, over 20 wt % $Ni/SiO_2$, 5 hours time on stream at 1 $hr^{-1}$ WHSV. For the heavy cut, the mixture was dissolved in hexane before feeding to the continuous flow reactor. The 2D-GC analysis of the result product is shown in FIG. 3C. As shown in the figure, the product mix comprised alcohols and diols.

Figure 4A:
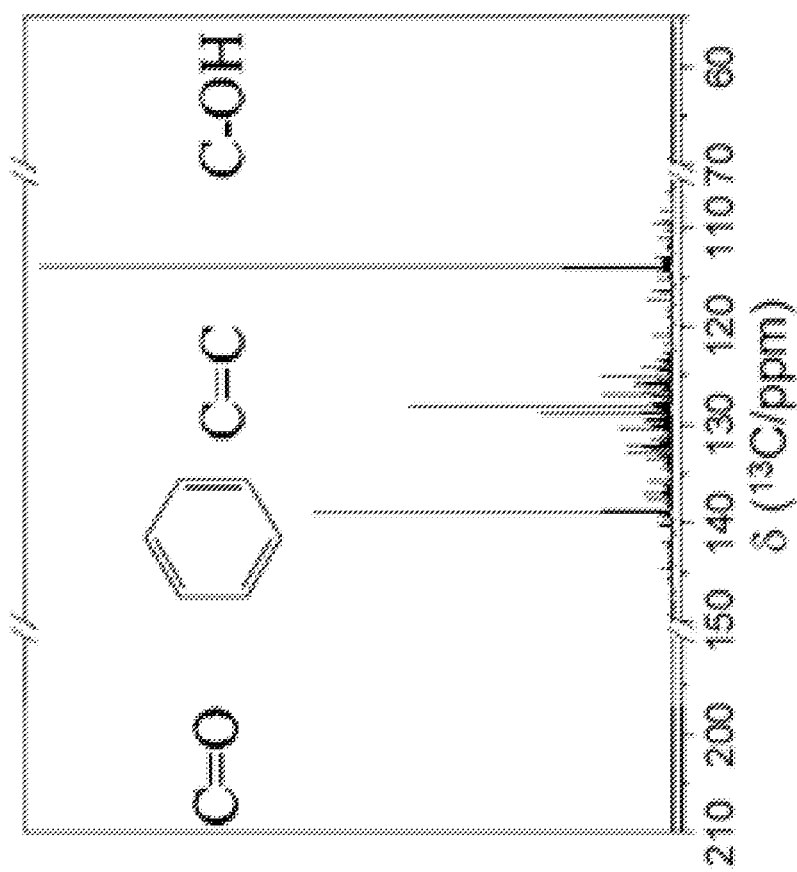
FIG. 4A is the $^{13}$C NMR spectrum of the light cut pyrolysis oil from FIG. 3A.
Figure 4B:
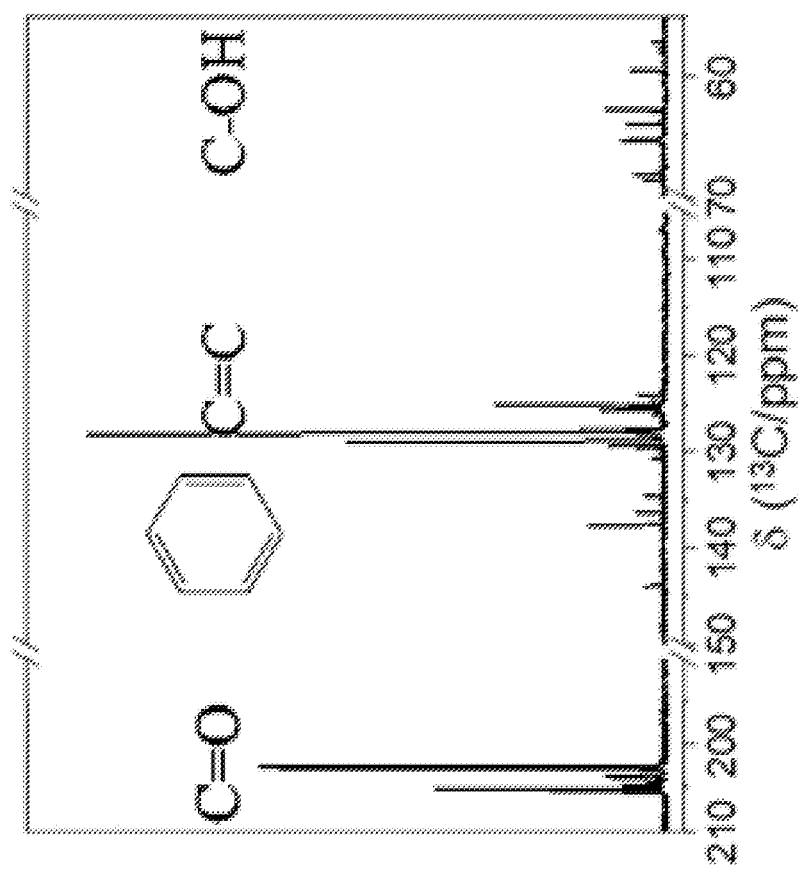
FIG. 4B is the $^{13}$C NMR spectrum of the product mix resulting from the light cut oil, post-hydroformylation, whose 2D-GC is shown in FIG. 3B.
Figure 4C:
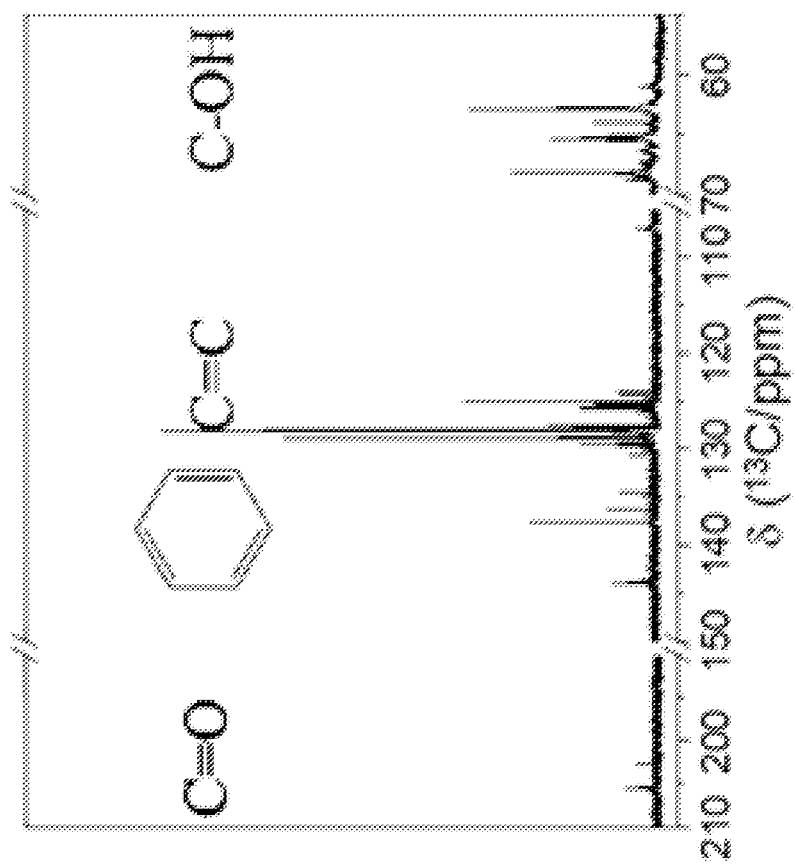
FIG. 4C is the $^{13}$C NMR spectrum of the product mix resulting from the light cut oil, post-hydrogenation, whose 2D-GC is shown in FIG. 3C.
Figure 4D:
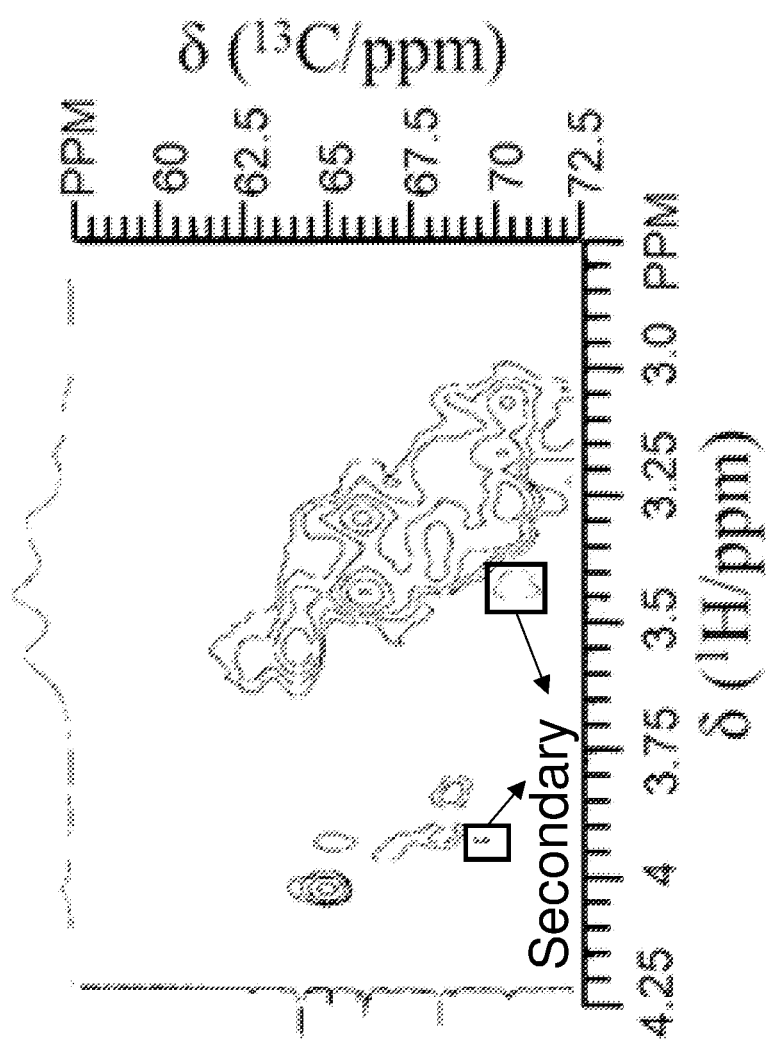
FIG. 4D shows the $^1$H-$^{13}$C heteronuclear single quantum coherence (HSQC) NMR spectrum of the product mix, post-hydrogenation, whose 2D-GC is shown in FIG. 3C.

FIG. 4A presents the $^{13}C$ NMR spectrum of the light cut pyrolysis oil from FIG. 3A. As shown, the light cut pyiolysis oil prior to further manipulation contained a very strong signal for aromatic compounds, but no detectable signal for carbonyl-containing compounds nor primary alcohols. FIG. 4B is the $^{13}C$ NMR spectrum of the same product mix, post-hydroformylation. (The corresponding 2D-GC is shown in FIG. 3B.) The comparison to FIG. 4A is immediately apparent. Whereas FIG. 4A has no signal for carbonyl compounds or alcohols, the $^{13}C$ NMR spectrum shown in FIG. 4B has very pronounced signals indicating the presence of aldehydes, and a less-pronounced, but still easily detectable set of signals indicated a small presence of alcohols. FIG. 4C is the $^{13}C$ NMR spectrum of the product mix resulting from the light cut oil, post-hydrogenation. (The corresponding 2D-GC is shown in FIG. 3C.). Here, the spectrum clearly shows that a very substantial portion of the aldehydes present in the mixture resulting from hydroformylation have been converted to alcohols. See the right-hand portion of FIG. 4C. FIG. 4D shows the $^{1}H$-$^{13}C$ heteronuclear single quantum coherence (HSQC) NMR spectrum of the product mix, post-hydrogenation, whose 2D-GC is shown in FIG. 3C. Signal assigned to secondary alcohols were labeled and the rest of the $^{1}H/^{13}C$ correlation signals belong to primary alcohols. This confirms the abundance of the primary alcohols.

Figure 5A:
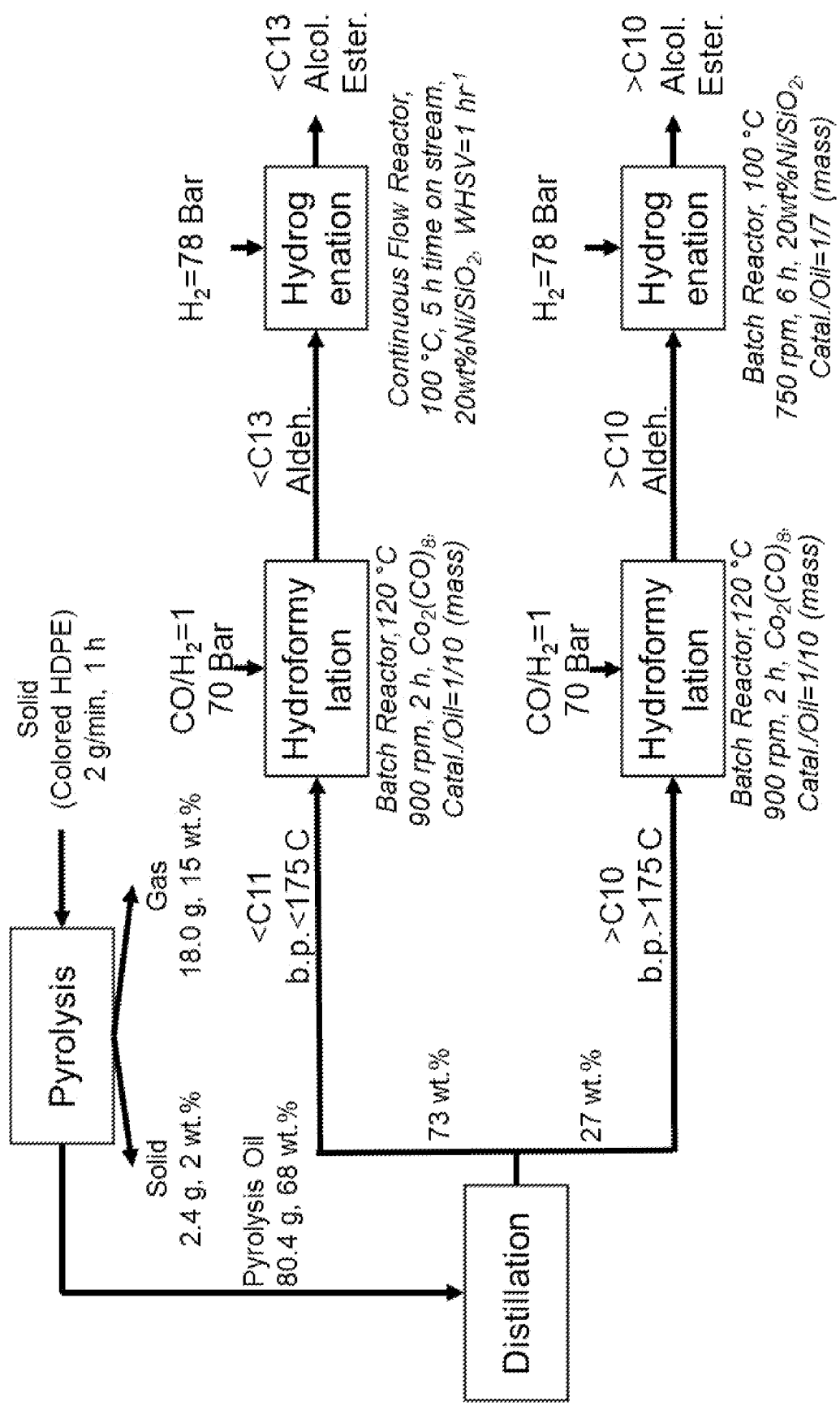
FIG. 5A is a process flow diagram for upcycling colored post-consumer waste, high-density polyethylene (HDPE) according to the present method. Here, after distillation into a light cut and a heavy cut (as described above), the two cuts are subjected to hydroformylation followed by hydrogenation to yield a light product mixture comprising alcohols having less than about 13 carbon atoms and a heavy product mixture comprising alcohols having more than about 10 carbon atoms. Exemplary reaction conditions are as stated in the figure.
Figure 5B:
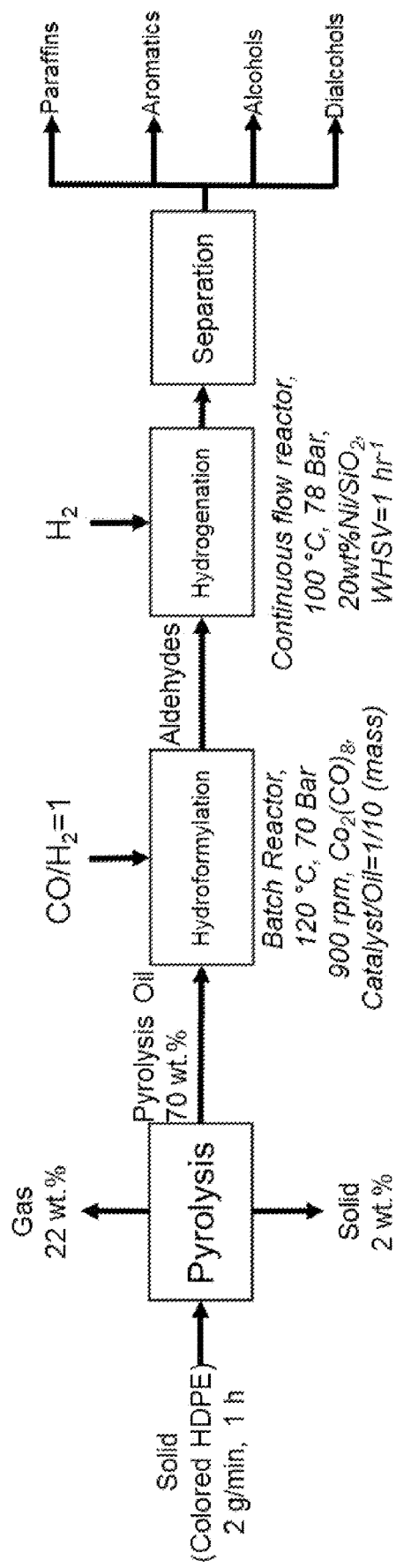
FIG. 5B is an alternative process flow diagram for upcycling colored post-consumer waste into paraffins, aromatics, alcohols, and/or di-alcohols using the method disclosed herein. Reaction conditions are as stated in the figure.

FIG. 5 shows an illustrative (exemplary) implementation of the method disclosed herein. Starting from the top of the figure, a feed stock of waste plastic, in this case colored post-consumer waste HDPE is subjected to pyrolysis to yield pyrolysis oil. 120 grams of the HDPE were introduced to a pyrolysis chamber set at 500° C. at a rate of 2 g/min (1 hour total feed time). The pyrolysis yielded 83.8 grams (70 wt %) of pyrolysis oil. The pyrolysis oil was then distilled into two fractions: a light fraction having a boiling point of less than about 175° C. (73 wt %) and a heavy fraction having a boiling point of more than about 175° C. (27 wt %). The light fraction was comprised mainly of compounds having about 11 carbon atoms or less. The heavy fraction was comprised mainly of compounds having more than 10 carbon atoms.

The light fraction was subjected to hydroformylation in a batch reactor under 70 Bar syngas (1:1; $H_2$:CO), for 3 hours, at 120° C. with vigorous stirring, and with $Co_2(CO)_8$ as the catalyst. The catalyst was loaded at a 1:10 wt ratio catalyst-to-pyrolysis oil. The resulting mixture was then subjected to hydrogenation. This was done in a continuous flow reactor at 78 Bar $H_2$. The reaction was performed using 20 wt % $Ni/SiO_2$ at 100° C., for 5 hours, at a WHSV of 1 $hr^{-1}$. The resulting product mix comprised alcohols having about 13 carbon atoms or less.

In an analogous fashion, the heavy fraction was subjected to hydroformylation in a batch reactor under 70 bar syngas (1:1; $H_2$:CO), for 3 hours, at 120° C. with vigorous stirring, and with $CO_2(CO)_8$ as the catalyst. The catalyst was loaded at a 1:12 wt ratio catalyst-to-pyrolysis oil. The resulting mixture was then subjected to hydrogenation. This was done in a continuous flow reactor at 78 Bar $H_2$. The reaction was performed using 20 wt % $Ni/SiO_2$, at 100° C., for 5 hours, at a WHSV of 1 $hr^1$. The resulting product mix comprised alcohols having about 10 carbon atoms or more.

Figure 6:
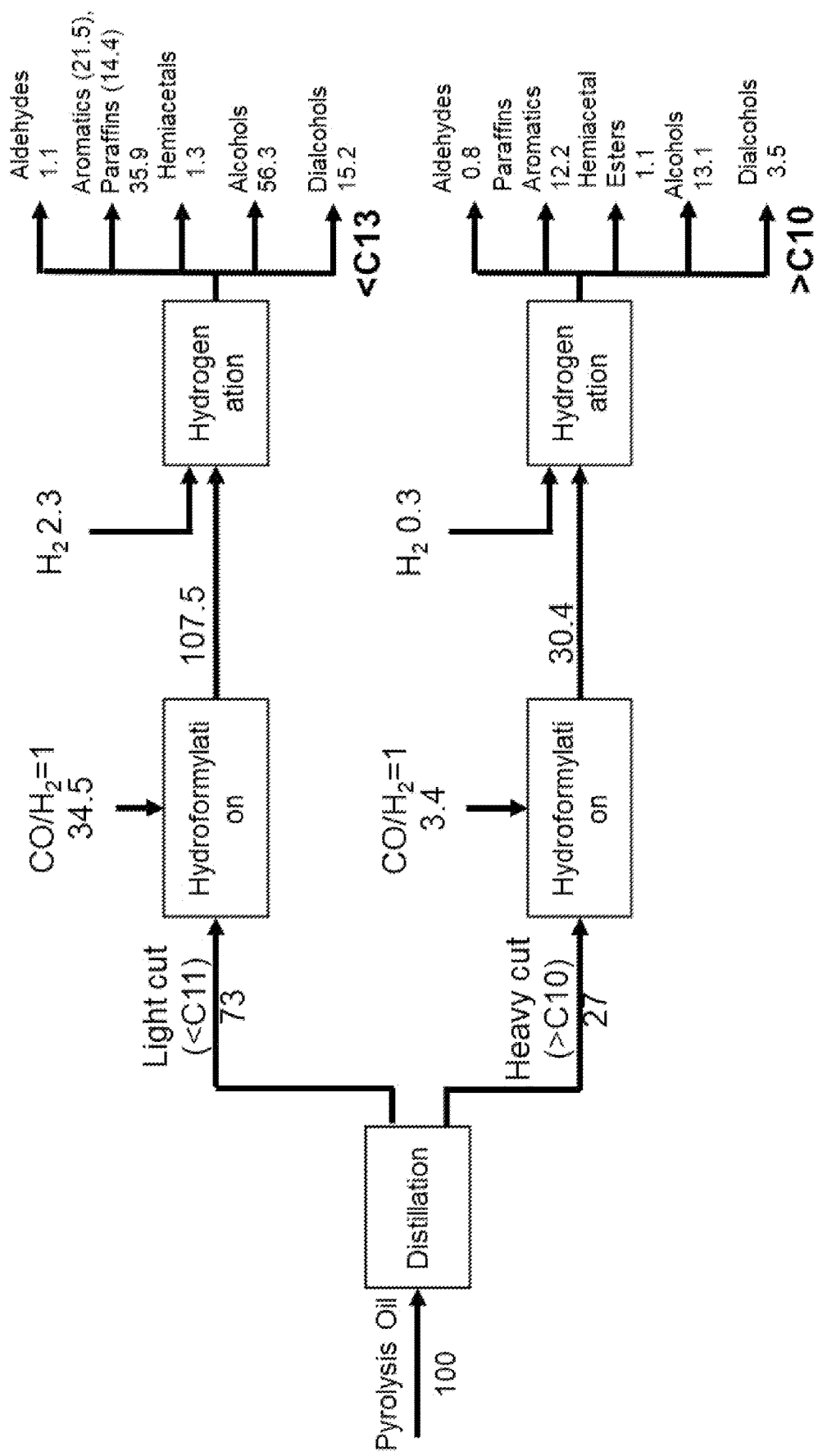
FIG. 6 is a detailed input-output analysis for upgrading pyrolysis oil made from waste plastics according to the method disclosed herein. The reactant was 100 g of pyrolysis oil, which was then distilled into light and heavy cuts as described previously. Each cut was then subjected to hydroformylation followed by hydrogenation. The light and heavy product mixtures comprised aldehydes, aromatics, paraffins, hemiacetals, esters, mono-alcohols, and di-alcohols in the amounts shown in the figure.
Figure 7A:
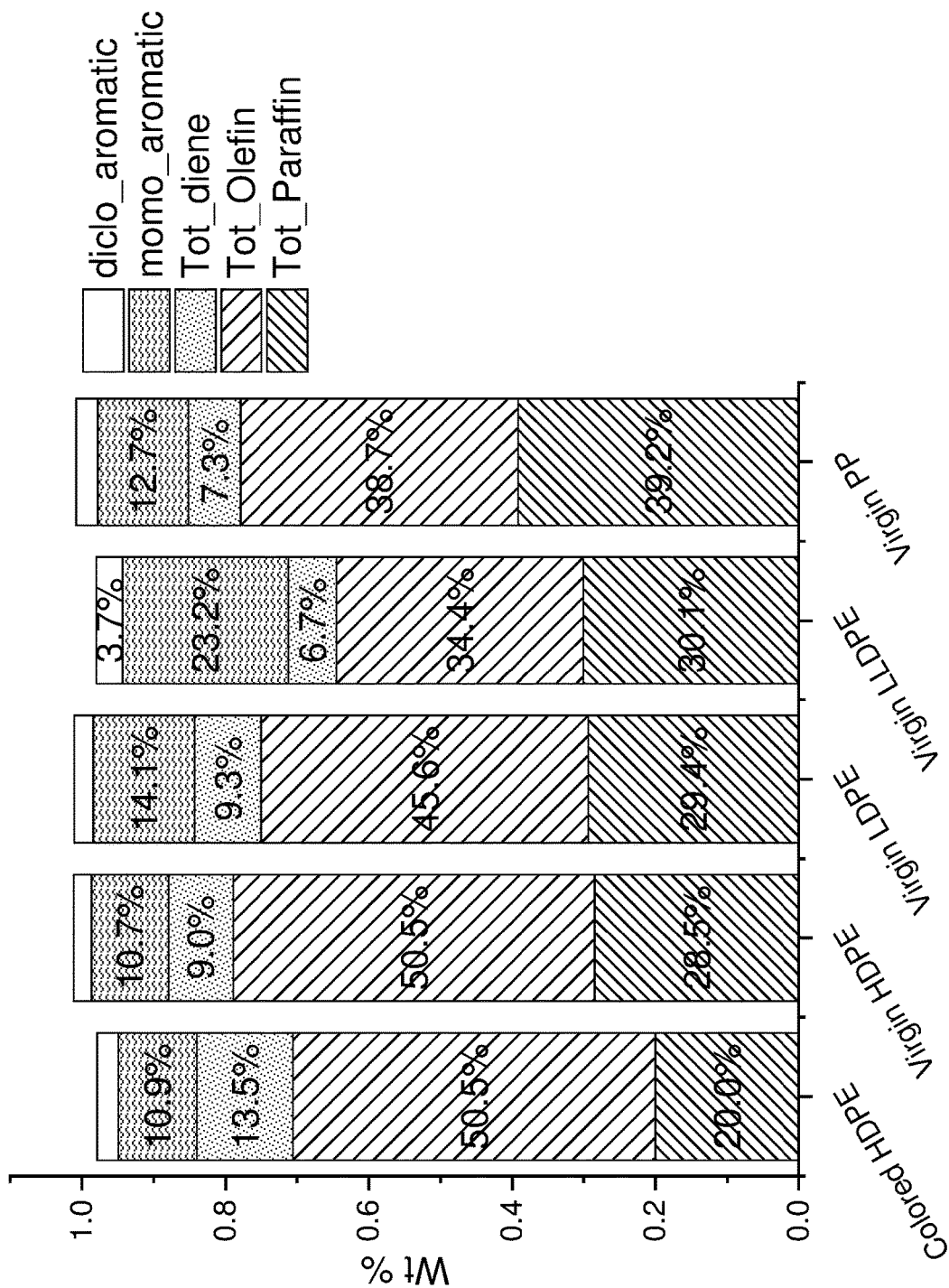
FIG. 7A is a histogram depicting product distributions found in different non-distilled polyolefin pyrolyzed oil (about C5 to about C40) feedstocks. Here, the pyrolysis oil was formed at 500° C. and 20 s residence time. HDPE has the highest yield of olefins and dienes among the plastic types pyrolyzed. With increasing branch density, more paraffins and aromatics are present. Thus, under the same pyrolysis conditions, a HDPE feedstock yields a less-branched pyrolysis oil and favors the formation of olefin and dienes.
Figure 7B:
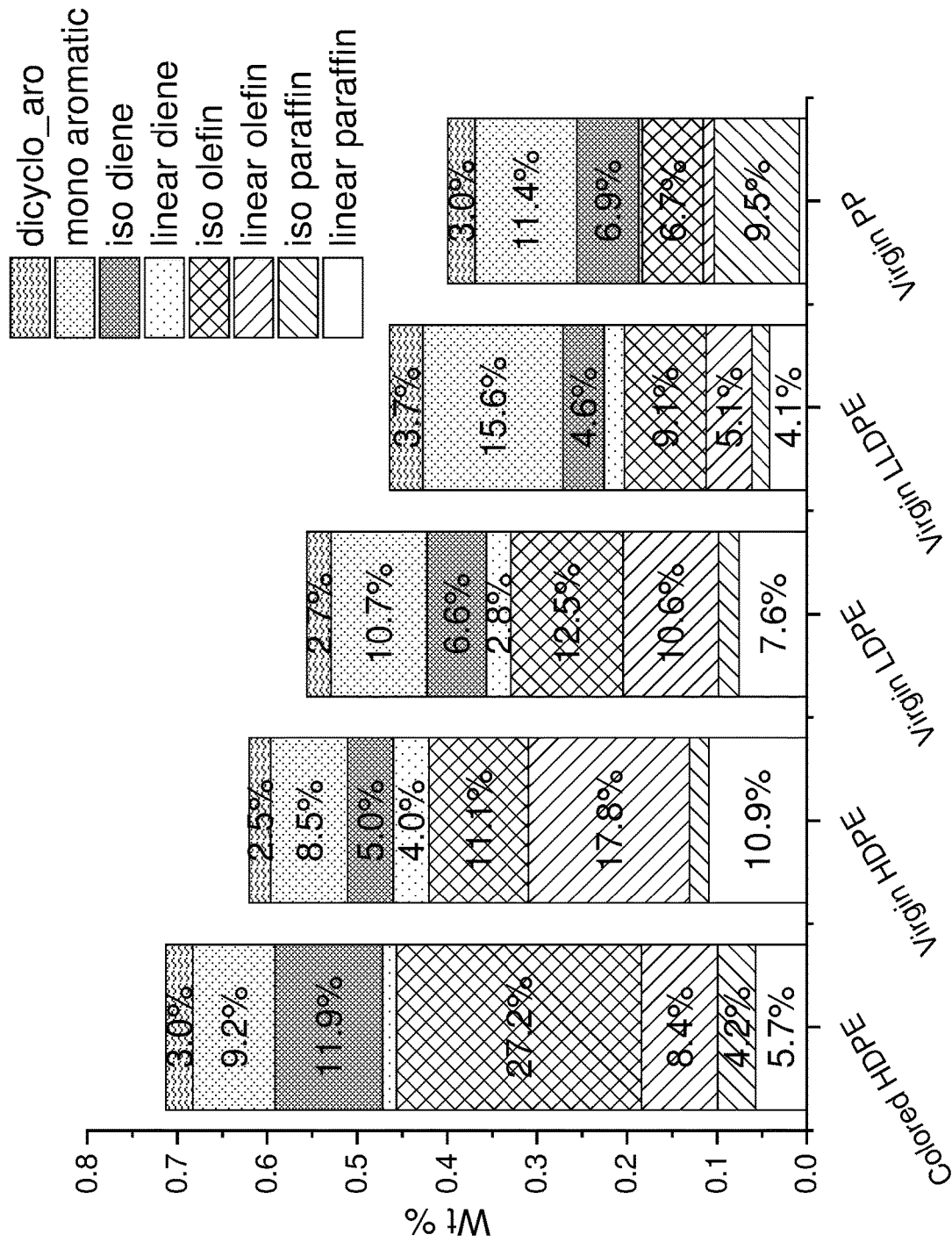
FIG. 7B is a histogram depicting product distributions found in non-distilled polyolefin pyrolyzed oil formed at 500° C. and 20 s residence time. The resulting pyrolysis oil contains products distributed from about C7 to C40. Virgin HDPE generates the most linear olefins and linear dienes among the plastics tested. Post-consumer waste HDPE (colored HDPE) oil contained less linear product than the virgin HDPE oil. Impurities or additives in the post-consumer waste HDPE likely caused isomerization of the linear hydrocarbons during the pyrolysis process.

FIG. 6 is a detailed input-output analysis for the reaction shown in FIG. 5 and described above. The reaction conditions were the same as those described in FIG. 5. The reactant was 100 g of pyrolysis oil, which was then distilled into light and heavy cuts as described previously. Each cut was then subjected to hydroformylation followed by hydrogenation as described previously. The light and heavy product mixtures both yielded final product mixtures (post-hydroformylation and post-hydrogenation) that comprised aldehydes, aromatics, paraffins, esters, mono-alcohols, and di-alcohols.

The ultimate product mix from the light cut, post-hydroformylation and post-hydrogenation, contained 1.1 g aldehydes, 35.9 g aromatics and paraffins, 1.3 g hemiacetals, 56.3 g alcohols, and 15.2 g di-alcohols. The hydroformylation reaction consumed 34.5 g of syngas. The hydrogenation reaction consumed 2.3 grams of hydrogen.

The ultimate product mix from the heavy cut, post-hydroformylation and post-hydrogenation, contained 0.8 g aldehydes, 12.2 g aromatics, olefins, and paraffins, 1.1 g hemiacetals and esters, 13.1 g alcohols, and 3.5 g di-alcohols. The hydroformylation reaction consumed 3.4 g of syngas. The hydrogenation reaction consumed 0.3 grams of hydrogen.

The invention claimed is:

1. A method to make primary alcohols, di-alcohols, or esters from plastic waste, the method comprising:
   (a) providing pyrolysis oil and separating the pyrolysis oil into a light cut having a boiling point less than about 175° C. and a heavy cut having a boiling point greater than about 175° C., where the light cut and the heavy cut comprise olefins, wherein the light cut consists essentially of compounds having less than 11 carbon atoms, and the heavy cut consists essentially of compounds having more than 10 carbon atoms; and then
   (b) hydroformylating the light cut and/or the heavy cut, independently, at a pressure between about 50 atm and about 70 atm and at a temperature between about 100° C. and 120° C., wherein at least a portion of the olefins in the light cut and/or the heavy cut are converted to aldehydes, to yield corresponding light and/or heavy mixtures comprising aldehydes;
   (c) separately hydrogenating the light mixture and/or the heavy mixture of step (b) to yield corresponding product mixture(s) comprising a product selected from the group consisting of primary alcohols, di-alcohols, esters, and combinations thereof.

2. The method of claim 1, wherein step (a) comprises providing pyrolysis oil from plastic waste comprising a poly(alkylene).

3. The method of claim 1, wherein step (a) comprises providing pyrolysis oil from plastic waste comprising poly (ethylene).

4. The method of claim 1, wherein step (b) comprises contacting the pyrolysis oil with syngas and a transition metal-containing catalyst.

5. The method of claim 4, wherein the transition metal-containing catalyst comprises cobalt or rhodium.

6. The method of claim 4, wherein the transition metal-containing catalyst comprises $HCo(CO)_4$, $Co_2(CO)_8$, a triphenylphosphine-modified cobalt-containing catalyst, a triphenylphosphine-modified rhodium-containing catalyst, a cobalt-containing salt of triphenylphosphinetrisulfonate, or a rhodium-containing salt of triphenylphosphinetrisulfonate.

7. The method of claim 4, wherein step (c) comprises contacting the mixture of step (b) with hydrogen and a transition metal-containing catalyst, for a time, at a temperature, and at a pressure of hydrogen wherein at least a portion of aldehydes contained in the mixture of step (b) are converted into alcohols.

8. The method of claim 4, wherein when step (c) is performed on the light cut, the product mixture comprises products having from 5 to 13 carbon atoms, and when step (c) is performed on the heavy cut, the product mixture comprises products having from 10 to 30 carbon atoms.

* * * * *